(12) United States Patent
Tweden et al.

(10) Patent No.: US 6,406,488 B1
(45) Date of Patent: *Jun. 18, 2002

(54) HEALING TRANSMYOCARDIAL IMPLANT

(75) Inventors: Katherine S. Tweden, Mahtomedi; Guy P. Vanney, Blaine, both of MN (US)

(73) Assignee: HeartStent Corporation, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/141,284

(22) Filed: Aug. 27, 1998

(51) Int. Cl.$^7$ ................................................. A61F 2/06
(52) U.S. Cl. ...................... 623/1.16; 623/1.4; 623/1.43
(58) Field of Search ........................... 623/1, 12, 1.15, 623/1.16, 1.42, 1.43, 1.44, 1.46, 1.13, 1.14, 1.39, 1.4; 606/194, 153; 604/8

(56) References Cited

U.S. PATENT DOCUMENTS

| | | | |
|---|---|---|---|
| 5,429,144 A | | 7/1995 | Wilk ........................... 128/898 |
| 5,449,373 A | * | 9/1995 | Pinchasik et al. .......... 623/12 X |
| 5,545,217 A | | 8/1996 | Offray et al. |
| 5,575,818 A | * | 11/1996 | Pinchuk ..................... 623/12 X |
| 5,655,548 A | | 8/1997 | Nelson et al. |
| 5,683,448 A | * | 11/1997 | Cragg ............................ 623/1 |
| 5,683,453 A | * | 11/1997 | Palmaz .......................... 623/1 |
| 5,693,085 A | | 12/1997 | Buirge et al. |
| 5,755,682 A | | 5/1998 | Knudson et al. ................ 604/8 |
| 5,824,040 A | * | 10/1998 | Cox et al. .................. 623/1.35 |
| 5,843,172 A | * | 12/1998 | Yan ................................ 623/1 |
| 5,855,598 A | * | 1/1999 | Pinchuk ..................... 623/1.13 |
| 5,948,018 A | * | 9/1999 | Dereume et al. ............... 623/1 |
| 5,984,956 A | | 11/1999 | Tweden et al. |

FOREIGN PATENT DOCUMENTS

| | | |
|---|---|---|
| WO | WO 97/27898 | 8/1997 |
| WO | WO 97/47651 | 12/1997 |
| WO | WO 98/06356 | 2/1998 |
| WO | WO 98/08456 | 3/1998 |
| WO | WO 98/16172 | 4/1998 |
| WO | WO 99/17683 | 4/1999 |

OTHER PUBLICATIONS

Carter, A. J. et al., "Éffects of Endovascular Radiation From a β–Particle—Emitting Stent in a Porcine Coronary Restenosis Model", *Circulation*, 94(10):2364–2368 (Nov. 15, 1996).

Flugelman, M. Y. et al., "Genetically Engineered Endothelial Cells Remain Adherent and Viable After Stent Deployment and Exposure to Flow In Vitro", *Circulation Research*, 70(2):.348–354 (Feb. 1992).

Schürmann, K. et al., "Iliac Arteries: Plain and Heparin—coated Dacron—covered Stent—Grafts Compared with Noncovered Metal Stents—An Experimental Study", *Radiology*, 203(1):55–63 (Apr. 1997).

Slepian, M. J. et al., $β_3$—Integrins Rather Than $β_1$—Integrins Dominate Integrin—Matrix Interactions Involved in Postinjury Smooth Muscle Cell Migration, *Circulation*, 97:1818–1827 (May 12, 1998).

* cited by examiner

*Primary Examiner*—Bruce Snow
*Assistant Examiner*—Brian E. Pellegrino
(74) *Attorney, Agent, or Firm*—Merchant & Gould P.C.

(57) ABSTRACT

A transmyocardial implant establishes a blood flow path through a myocardium between a heart chamber and a lumen of a coronary vessel residing on an exterior of the heart. The implant includes a coronary portion sized to be received within the vessel. A myocardial portion is sized to pass through the myocardium into the heart chamber. A transition portion connects the coronary and myocardial portions for directing blood flow from the myocardial portion to the coronary portion. The coronary portion and the myocardial portion have an open construction for permitting tissue growth across a wall thickness of the coronary portion and the myocardial portion. The myocardial portion includes an agent for controlling a coagulation cascade and platelet formation.

14 Claims, 2 Drawing Sheets

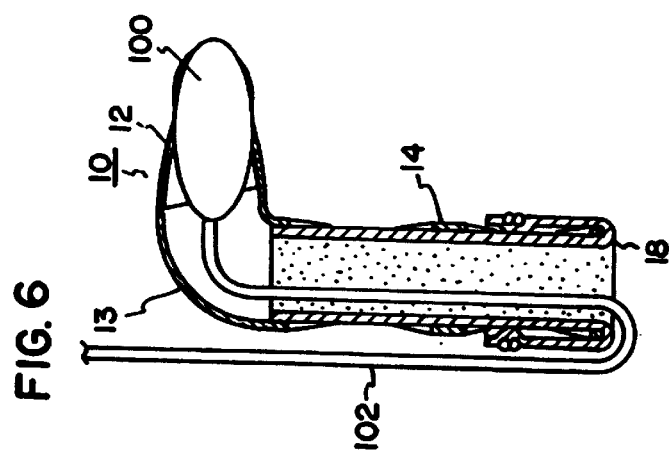
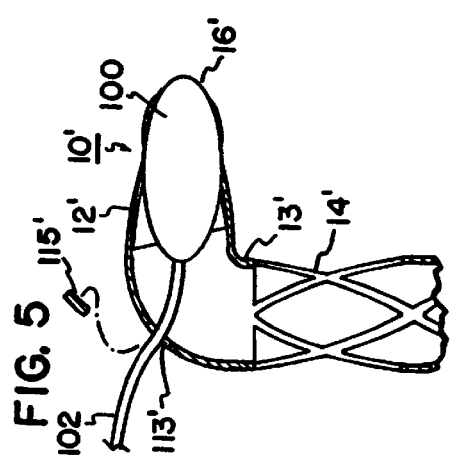
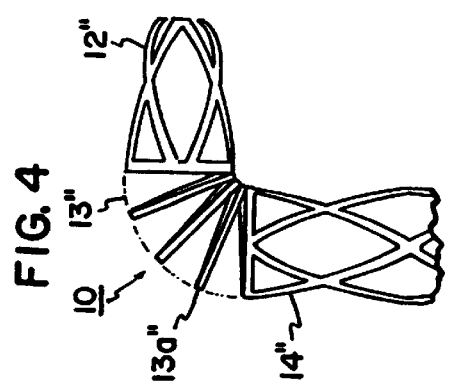

HEALING TRANSMYOCARDIAL IMPLANT

BACKGROUND OF THE INVENTION

1. Field of the Invention

This invention pertains to an implant for passing blood flow directly between a chamber of the heart and a coronary vessel. More particularly, this invention pertains to such an implant with an enhance design for promoting a healed layer of cells on an interior of the implant.

2. Description of the Prior Art

Commonly assigned U.S. Pat. No. 5,755,682 issued May 26, 1998 and commonly assigned and co-pending U.S. patent application Ser. No. 08/882,397 filed Jun. 25, 1997, entitled "Method and Apparatus for Performing Coronary Bypass Surgery", and filed in the name of inventors Mark B. Knudson and William L. Giese (published as PCT International Application Publication No. WO 98/06356) both teach an implant for defining a blood flow conduit directly from a chamber of the heart to a lumen of a coronary vessel. In one embodiment, an L-shaped implant is received within a lumen of a coronary artery and passed through the myocardium to extend into the left ventricle of the heart. The conduit is rigid and remains open for blood flow to pass through the conduit during both systole and diastole. The conduit penetrates into the left ventricle in order to prevent tissue growth and occlusions over an opening of the conduit. The '682 patent and '397 application also describe an embodiment where a portion of the implant passing through the heart wall is an open structural member lined by polyester (e.g., Dacron). A further embodiment discloses a portion of the implant in a coronary vessel as being an open cell, balloon-expandable stent.

U.S. Pat. No. 5,429,144 to Wilk dated Jul. 4, 1995 teaches implants which are passed through the vasculature in a collapsed state and expanded when placed in the myocardium so as not to extend into either the coronary artery or the left ventricle. The described implants close once per cycle of the heart (e.g., during diastole in the embodiment of FIGS. 7A and 7B or during systole in the embodiment of FIGS. 2A and 2B). Either of these two designs may be lined with a graft.

Commonly assigned and co-pending U.S. patent application Ser. No. 08/944,313 filed Oct. 6, 1997, entitled "Transmyocardial Implant", and filed in the name of inventors Katherine S. Tweden, Guy P. Vanney and Thomas L. Odland, teaches an implant such as that shown in the aforementioned '397 application and '682 patent with an enhanced fixation structure. The enhanced fixation structure includes a fabric surrounding at least a portion of the conduit to facilitate tissue growth on the exterior of the implant.

PCT International Application Publication No. WO 98/08456 describes a protrusive stent to form a passageway from the heart to a coronary vessel. The stent is described as wire mesh or other metal or polymeric material and may be self-expanding or pressure expandable. The application describes the stent may be covered by a partial or complete tubular covering of material including polyester, woven polyester, polytetraflouroethylene, expanded polytetraflouroethylene, polyurethane, silicone, polycarbonate, autologous tissue and xenograft tissue.

Biocompatibility is an important design feature. Solid metal implants are formed of material (e.g., titanium or pyrolytic carbon) with low incidents of thrombus and platelet activation. While such materials are proven in use in a wide variety of products (e.g., heart valve components), they do not facilitate fall healing. By "healing", it is meant that over time, the patient's cells grow over the material of the implant so that blood flowing through the implant is exposed only (or at least primarily) to the patient's cells rather than to a foreign material.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. The implant includes a coronary portion sized to be received with the vessel. A myocardial portion is sized to pass through the myocardium into the heart chamber. A transition portion connects the coronary and myocardial portions for directing blood flow from the myocardial portion and into the coronary portion. The coronary portion and the myocardial portion have an open construction for permitting tissue growth across a wall thickness of the coronary portion and the myocardial portion. The myocardial portion includes an agent for controlling the coagulation cascade and platelet activation, and promoting healing.

BRIEF DESCRIPTION OF THE DRAWINGS

FIG. 4 is a view similar to FIG. 3 showing a transition portion of open cell construction;

FIG. 5 is a side section view of an alternative embodiment of FIG. 3 showing a balloon catheter admitted into the implant through an access port; and FIG. 6 is a side sectional view of an expandable implant with a balloon catheter removable through a myocardial portion of the catheter.

DESCRIPTION OF THE PREFERRED EMBODIMENT

Figure 1:
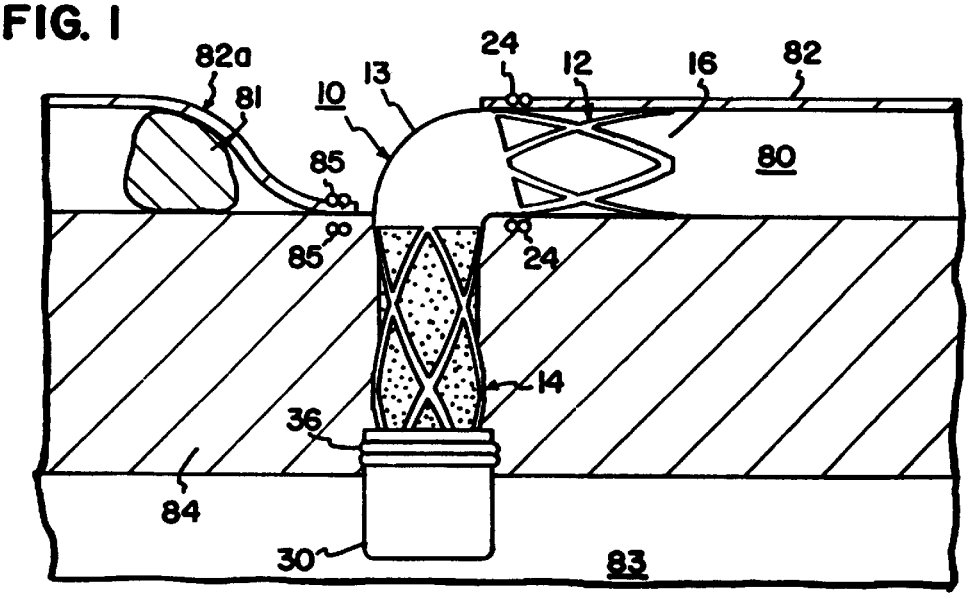
FIG. 1 is a side-elevation view of a transmyocardial implant according to the present invention shown in place defining a blood flow path from a left ventricle to a coronary artery.
Figure 2:
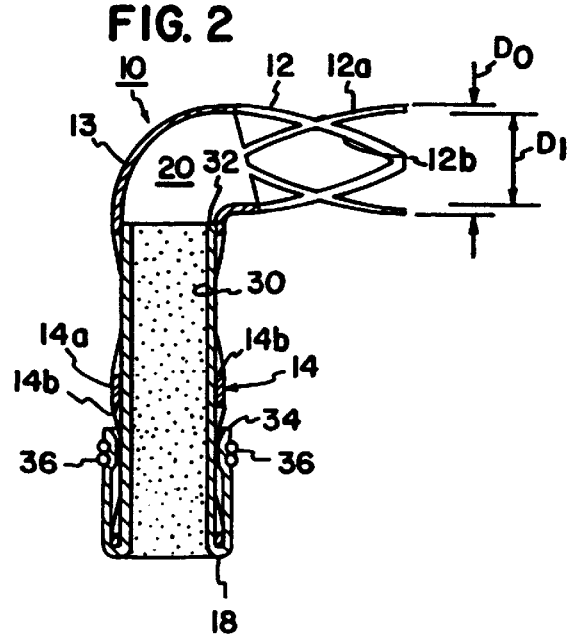
FIG. 2 is a cross-sectional view of the implant of FIG. 1.

With initial reference to FIG. 1, a conduit 10 is shown in the form of an L-shaped tube. The conduit 10 may be formed of titanium or other biocompatible material. The material of the conduit 10 is preferably radially rigid material in order to withstand contraction forces of the myocardium. By way of non-limiting example, the tube will have an outside diameter $D_O$ of about 3 millimeters and an internal diameter $D_I$ of about 2.5 millimeters to provide a wall thickness of about .25 millimeters.

The tube 10 has a coronary portion 12 sized to be received within the lumen of a coronary vessel such as the lumen 80 of a coronary artery 82 distal to an obstruction 81 as illustrated in FIG. 1. The conduit 10 has a myocardial portion 14 extending at a right angle to the axis of portion 12. The myocardial portion 14 is sized to extend from the coronary artery 82 directly through the myocardium 84 and protrude into the left ventricle 83 of a patient's heart.

The coronary portion 12 has a first opening 16. The myocardial portion 14 has a second opening 18 in communication with an interior 20 of the implant 10. Therefore, blood can freely flow through the implant 10 between the left ventricle 83 and the lumen 80 of the coronary artery 82. Blood flows axially out of opening 16 parallel with the axis of lumen 80.

The longitudinal axis of the coronary portion 12 is aligned with the axis of the lumen 80. Sutures 24 secure the artery 82 to the coronary portion 12. The proximal portion 82a of the coronary artery is ligated by sutures 85.

The coronary and myocardial portions 12, 14 have an open lattice construction 12a, 14a to define a plurality of open cells 12b, 14b extending through the wall thickness of the implant 10. Preferably, the coronary and myocardial portions 12, 14 are joined by a transition portion 13 in a 90° bend between portions 12, 14. While transition portion 13 can have an open lattice construction as portions 12, 14, transition portion 13 will preferably have smaller open areas in such an open construction or, as illustrated, will be of solid construction. Such construction permits the transition portion to deflect high velocity blood flows from the myocardial portion 14 into the coronary portion 12. A lattice construction with large open cells in the transition portion could result in the high velocity flow damaging tissue (not shown) overlying the transition portion.

Figure 3:
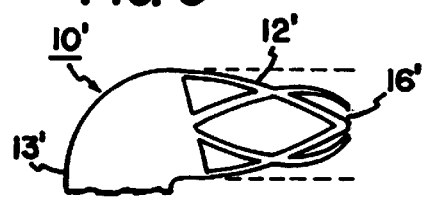
FIG. 3 is a view of an alternative embodiment of the implant of FIG. 1 illustrating a portion of the implant expandable within a coronary artery.

Any one or all of the coronary portion 12, transition portion 13 and myocardial portion 14 could be formed in final size as rigid units or could be formed in small diameter sizes which are subsequently expanded to full size. For example, FIG. 3 illustrates a coronary portion 12' which is formed tapering from the transition portion 13' to a reduced diameter open end 16'. The taper permits ease of insertion into a coronary artery. Following such insertion, the tapered coronary portion 12' may be expanded to full size illustrated by the phantom lines in FIG. 3. Such expansion can be performed using balloon-tipped catheters as is conventional in stent angioplasty. A collapsed and subsequently expanded implant 10 where all portions 12, 13 and 14 are expanded can permit use as a percutaneously deployed implant. The present drawings illustrate a presently preferred surgically deployed implant. In the surgical application, the artery is ligated. The implant 10 is passed through the epicardium and myocardium on a side of the artery 82.

FIG. 5 illustrates a balloon 100 placed in a tapered coronary portion 12. A lead 102 from the balloon 100 is passed through an opening 113' in the transition portion 13'. The opening 113' can be closed with a plug 115' after the balloon 100 and lead 102 are withdrawn through the opening 113'.

Alternatively, in a transition portion 13" with open cell construction (FIG. 4), the balloon lead can be passed through the openings of the transition portion 113". FIG. 6 illustrates passing the lead 102 through opening 18 of the myocardial portion. The lead 102 can be pulled upwardly from the exterior of the heart to remove the balloon 100. Alternatively, the lead 102 can be pulled through a catheter (not shown) adjacent end 18 in the left ventricle.

In either percutaneous or surgical implants, a flexible transition portion 13 (as would be achieved with a stent lattice construction) permits relative articulation between the coronary and myocardial portions 12, 14 to ensure the coronary portion is axially aligned with the lumen 80. Absent such articulation, such axial alignment is achieved by accurately controlling the position of the myocardial portion 14 such that the coronary portion 12 is axially aligned with the lumen 80 following implantation.

The open cell construction of the coronary and myocardial portions 12, 14 permit tissue growth through the open cells 12b, 14b following implant. The healing procedure in the coronary portion 12 is the same as that in coronary stents. Vascular endothelial cells grow over to coat the structural material 12a of portion 12.

In portion 14, myocardial tissue, if not obstructed, will grow through the cells 14b. Furthermore, the myocardium is highly thrombogenic. Therefore, uncontrolled contact between the myocardium 82 and the implant interior 20 can result in thrombosis of the implant 10. Further, it is believed that the epicardium (i.e., outer layer of the myocardium) has a greater density of myocardial growth cells which contribute to healing.

To control growth in the myocardial portion 14, a liner 30 is provided in the myocardial portion 14. The liner 30 is any porous material for accepting tissue growth and, preferably, is a polyester fabric (e.g., Dacron). The porous liner 30 has interstitial spaces smaller than the open cells 12c, 14c. The liner 30 is shown on an interior of the myocardial portion 14 but could also or alternatively surround the exterior.

The liner 30 has an upper end 32 secured through any suitable means (e.g., sutures not shown) to the upper end of the myocardial portion 14. A lower end 34 is folded over the opening of the myocardial portion 14 and secured to the exterior of the portion 14 by sutures 36. The myocardial portion 14 is sized to protrude into the left ventricle 83 with only the folded over liner material exposed to the interior of the left ventricle 83.

The liner 30 acts as a porous substrate into which tissue may grow. To prevent thrombus, the liner 30 is impregnated with an agent for controlling coagulation cascade and platelet activation and adhesion. An example of such an agent is heparin but could be any anticoagulant or anti-platelet. Also, an agent such as a basic fibroblast growth factor could be used to accelerate healing.

The agent permits structural cells to grow on the liner by limiting thrombus formation which, uncontrolled, would occlude the implant. Due to the open construction, the structural, healing cells of the epicardium can grow onto the liner. Subsequently, endothelial cells can grow on the structural cells.

Therefore, the structure described promotes a three-stage healing process:
1. the drug agents control healing by minimizing coagulation and platelet activation which would otherwise be stimulated by agents from the myocardium; and
2. structural cells grow into and on the liner 30 now lined with the thrombus to initially heal and form a vascular bed; and
3. endothelial cells grow over the structural cells.

In the transition portion 13, an open cell structure will permit tissue growth as in the coronary portion 12. Such growth may also occur in the solid construction. Alternatively, the liner 30 can be extended into the transition portion 13. Additionally, the open cell structure in the transition portion 13 can permit articulation between the coronary portion and the myocardial portion. Such a structure is shown in FIG. 4. The open transition portion 13" is formed by a coil 13a" between the coronary portion 12" and the myocardial portion 14". This structure permits bending at the transition portion. As a result, the coronary portion can be axially aligned in the artery without first accurately positioning the myocardial portion.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto. For example, the liner 30 can take many constructions including PTFE, expanded-PTFE, polyurethane, polypropylene or any biologically compatible paving material (e.g., a biologically compatible coating such as hydrogel coatings, for example, polyethylene oxide) or natural tissue. Further, restenosis of the coronary portion 12 can be prevented with radioactivity therapy (such as providing the coronary portion with a short half-life beta emitter). Also, the liner 30 may be either a resorbable or non-resorbable material. Genetically engineered cells can be transformed to secrete anticoagulants and other agents to keep the blood fluid (such as tissue plasminogen activator and smooth muscle cells altered to express nitric acid).

What is claimed:

1. A transmyocardial implant for defining a blood flow pathway directly from a left ventricle through a heart wall to a coronary vessel, the implant comprising:

a coronary portion sized to be received within the vessel;

a myocardial portion sized to pass through the myocardium into the left ventricle;

a transition portion connecting the coronary and myocardial portion for directing blood flow from the myocardial portion and into the coronary portion;

at least the coronary portion and the myocardial portion having an open construction for permitting tissue growth across a wall thickness of the coronary portion and the myocardial portion;

the myocardial portion including an agent for controlling a coagulation cascade and platelet activation;

a porous lining covering the myocardial portion with the porous lining having pores smaller than openings of the open construction of the myocardial portion, the porous lining having a length substantially equal to a width of the heart wall; and the porous lining covering at least the open construction of the myocardial portion but not the open construction of the coronary portion.

2. An implant according to claim 1 further comprising an agent for encouraging healing.

3. An implant according to claim 2 wherein the agent for encouraging healing is a growth factor.

4. An implant according to claim 1 wherein the porous lining contains the agent.

5. An implant according to claim 1 wherein the agent is heparin.

6. An implant according to claim 1 wherein the agent is an anti-coagulant.

7. An implant according to claim 1 wherein the agent is an anti-platelet.

8. An implant according to claim 1 wherein the coronary portion is expandable from a first diameter to an enlarged second diameter.

9. An implant according to claim 1 wherein the myocardial portion is expandable from a first diameter to an enlarged second diameter.

10. An implant according to claim 1 wherein the transition portion permits articulation between the coronary portion and the myocardial portion.

11. An implant according to claim 1 wherein the porous lining is constructed of a polyester fabric.

12. An implant according to claim 11 wherein the porous lining is constructed of Dacron.

13. An implant according to claim 1 wherein the porous lining is constructed on the interior portion of the open construction of the myocardial portion.

14. An implant according to claim 1 wherein the transition portion is of solid construction.

\* \* \* \* \*